(12) United States Patent
Nakamura

(10) Patent No.: US 8,440,466 B2
(45) Date of Patent: May 14, 2013

(54) NITROGEN OXIDE ANALYZER AND METHOD FOR SETTING PARAMETER APPLIED TO NITROGEN OXIDE ANALYZER

(75) Inventor: Hiroshi Nakamura, Kyoto (JP)

(73) Assignee: Horiba, Ltd., Kyoto (JP)

(*) Notice: Subject to any disclaimer, the term of this patent is extended or adjusted under 35 U.S.C. 154(b) by 1056 days.

(21) Appl. No.: 11/278,609

(22) Filed: Apr. 4, 2006

(65) Prior Publication Data

US 2006/0223190 A1    Oct. 5, 2006

(30) Foreign Application Priority Data

Apr. 4, 2005 (JP) ................................ 2005-107865

(51) Int. Cl.
G01N 21/76    (2006.01)
G01N 33/00    (2006.01)

(52) U.S. Cl.
USPC .............. 436/118; 422/52; 436/106; 436/116; 436/117; 436/172

(58) Field of Classification Search ............ 422/52; 436/106, 116–118, 172
See application file for complete search history.

(56) References Cited

U.S. PATENT DOCUMENTS

| 3,882,028 | A | 5/1975 | Zolner |
| 4,822,564 | A * | 4/1989 | Howard ........................ 422/52 |
| 6,207,460 | B1 * | 3/2001 | Kishkovich et al. ......... 436/106 |
| 2002/0137227 | A1 * | 9/2002 | Weckstrom .................... 436/172 |
| 2002/0137228 | A1 * | 9/2002 | Weckstrom .................... 436/172 |
| 2003/0007908 | A1 * | 1/2003 | Han et al. ................. 422/186.07 |
| 2005/0199484 | A1 * | 9/2005 | Olstowski .................... 204/176 |

FOREIGN PATENT DOCUMENTS

| JP | 61-151446 A | 7/1986 |
| JP | 63-5242 A | 1/1988 |
| JP | 63-317747 A | 12/1988 |
| JP | 4-264239 | * 9/1992 |
| JP | 6-167450 A | 6/1994 |
| JP | 7-301603 | * 11/1995 |
| JP | 2000-35402 A | 2/2000 |
| JP | 2001-153857 A | 6/2001 |
| JP | 2002-5838 | 1/2002 |
| JP | 2004-45297 A | 2/2004 |

OTHER PUBLICATIONS

DeCarteret et al. Optimization of a commercially available chemiluminescent analyzer for low level NOx measurement. Society of Automotive Engineers, [Special Publication] SP (2003), SP-1757 (Emission Measurement & Testing 2003). pp. 23-26. (2003).*
Boulter et al. Chapter 13: Gas-Phase Chemiluminescence Detection. Chemiluminescence in Analytical Chemistry. pp. 349-374. (2001).*
Ridley, B. A. et al, Review of Scientific Instruments 1974, 742-746.*

(Continued)

Primary Examiner — Arlen Soderquist
(74) Attorney, Agent, or Firm — Brooks Kushman P.C.

(57) ABSTRACT

The nitrogen oxide analyzer obtains the ozone concentration-luminescence response characteristics that show the relationship between the ozone concentration and the light intensity by chemiluminescent response obtained by varying the ozone concentration alone in a steady state, and sets the relationship of the parameter that determines an average period of the sample gas passing the reactor so that the luminescence response is generated in the reactor alone even though the ozone concentration of the ozone-containing gas changes within a predetermined range based on the ozone concentration-luminescence response characteristics.

8 Claims, 4 Drawing Sheets

OTHER PUBLICATIONS

Steffenson, D. M. et al, Analytical Chemistry 1974, 46, 1704-1709.*
Mehrabzadeh, A. A. et al, Analytical Chemistry 1983, 55, 1660-1665.*
Sigsby, J. E. et al, Environmental Science and Technology 1973, 7, 51-54.*
Black, F. M. et al, Environmental Science and Technology 1974, 8, 149-152.*
Matthews, R. D. et al, Environmental Science and Technology 1977, 11, 1092-1096.*
Michael, J. V. et al, Journal of Physical Chemistry 1981, 85, 4109-4117.*
Kaufman M., Journal of the American Chemical Society 1989, 111, 6901-6905.*
Combs, M. T. et al, Analytical Chemistry 1997, 69, 3044-3048.*

* cited by examiner

NITROGEN OXIDE ANALYZER AND METHOD FOR SETTING PARAMETER APPLIED TO NITROGEN OXIDE ANALYZER

BACKGROUND OF THE INVENTION

1. Field of the Invention

This invention relates to a nitrogen oxide analyzer that measures the concentration of nitrogen oxide contained in exhaust gas from vehicles.

2. Background Art

A chemiluminescent nitrogen oxide analyzer (hereinafter also called as a CLD type $NO_x$ analyzer) has been known as a device to continuously measure the concentration of nitrogen oxide ($NO_x$) in a time-series order. As shown by the following equation, the CLD type $NO_x$ analyzer measures an amount (the concentration) of $NO_x$ by converting $NO_x$ into NO, mixing ozone into NO, and detecting the intensity of light emitted at a time when excitation nitrogen dioxide that is generated when ozone is mixed into NO returns to a base state.

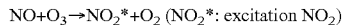

$NO+O_3 \rightarrow NO_2^* + O_2$ ($NO_2^*$: excitation $NO_2$)

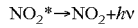

$NO_2^* \rightarrow NO_2 + h\nu$

More concretely, gas containing ozone and sample gas containing NO as being an object to be measured are introduced into a reactor and mixed there, and the intensity of the light generated due to a chemiluminescent response in the reactor is detected by a photoelectron multiplier or a photo detector such as a CCD. Conventionally, the gas containing ozone used is gas introduced from an ozone steel bottle or gas containing ozone of a certain degree of the concentration that is converted from oxygen in dehumidified atmospheric air by an ozone generator. (Japan Patent Laid-open Number 2002-5838.)

However, in a method of using the ozone steel bottle, a device becomes extremely grand-scale and the steel bottle has to be exchanged periodically. In addition, in a method of using the ozone generator, a dehumidifier or a drier is required in order to stabilize the concentration of oxygen (the concentration of ozone) by removing moisture of the atmospheric air. This method requires a periodic exchanging of the dehumidifier or the drier. In addition to this, an electric consumption is increased.

As a result, it is difficult for conventional devices to realize downsizing, electric power saving or maintenance-free, which becomes a bottleneck to realize a vehicle-mountable chemiluminescent nitrogen oxide analyzer.

If ozone-containing gas is generated by introducing the atmospheric air directly to the ozone generator without using a dehumidifier, it is possible to realize reduction of electric power, downsizing, or maintenance-free at once. However, since humidity in the atmospheric air is unstable, the concentration of ozone also becomes unstable. This might cause a detection error.

This is because the concentration of ozone is significantly involved in generation speed of excitation $NO_2$, in other words the light emitting period of excitation $NO_2$. If the concentration of ozone is low, the generation speed of excitation $NO_2$ becomes slow and the light emitting period becomes long. Then the light emission fails to be completed while the mixed gas is retained in a reactor. As a result, the light intensity detected in the reactor fails to be proportional to the concentration of excitation $NO_2$, resulting in the detection error (If the concentration of ozone is constant, a relationship between the light intensity in the reactor and the concentration of NO is one-on-one so that the concentration of NO can be shown whether or not the light emission is completed during the mixed gas is retained in the reactor, although detection sensitivity differentiates a little. As a result, the NO concentration can be measured with high accuracy as far as an analytical curve is obtained accurately).

As a result of this, in order to measure the concentration of NO accurately by the use of ozone-containing gas of unstable concentration, cubic volume or pressure of the reactor or a gas flow rate has to be set so that the light emission is completed in the reactor without fail and a property of space-saving is not lost, and time characteristics of a chemiluminescent response that is intrinsic to the system has to be known.

However, it is not easy to obtain the cubic volume or the pressure of the reactor or the gas flow rate theoretically because path resistance or other factor is intertwined. Although a batch method has been proposed as a method to obtain them by a test, a complicated mechanism or software is still required. It is very much a situation that a practical application by applying the complicated mechanism or software to various different analyzers is a long time on the way.

SUMMARY OF THE INVENTION

The present claimed invention first focuses on a fact that a relationship between the concentration of ozone and a chemiluminescent response where no function of time is included at all (ozone concentration-luminescence response characteristics) is used in order to obtain a time characteristic of a light emitting response intrinsic to a system. This invention intends to make it possible to generate ozone-containing gas by introducing atmospheric air directly to an ozone generator and to set parameters such as cubic volume of the reactor, pressure in the reactor and a gas flow rate to be tailored to any model so that light emission is completed in the reactor without fail in spite of using ozone-containing gas whose ozone concentration is unstable.

The present claimed invention is applied to a nitrogen oxide analyzer that comprises a reactor where ozone-containing gas and sample gas continuously introduced in a time-series order are mixed and the mixed gas is passed out through an output port, and a photo detector that detects the light intensity of chemiluminescence from the response between the ozone-containing gas and the sample gas in the reactor, wherein the concentration of nitrogen oxide in the sample gas can be calculated based on the light intensity detected by the photo detector.

And the present claimed invention is characterized by flowing reference sample gas containing nitrogen oxide with constant concentration and reference ozone gas with known concentration at a constant flow rate instead of the above-mentioned sample gas and the ozone-containing gas, respectively, generating a steady state with the pressure in the reactor kept constant, varying only the concentration of ozone in the steady state, obtaining ozone concentration-luminescence response characteristics that show a relationship between the ozone concentration and the light intensity by chemiluminescent response obtained by varying ozone concentration alone, and obtaining a relationship of a parameter that determines an average resident time of the sample gas in the reactor so that the luminescence response is almost completed in the reactor even though the ozone concentration of the ozone-containing gas varies within a predetermined range based on the ozone concentration-luminescence response characteristics.

In accordance with this arrangement, it is possible to produce the ozone-containing gas by directly importing the atmospheric air to the ozone generator without dehumidification and to set a parameter that designs, for example, the cubic volume of the reactor to be the least within a range wherein an accurate measurement can be conducted in spite of fluctuation of the ozone concentration.

As a result, power-saving or downsizing due to omission of the dehumidifier or the drier can be realized. This makes it possible to provide a real time nitrogen oxide analyzer especially very preferable for a vehicle-mountable use.

In addition, it is not so much difficult to create the steady state, and it is easy to obtain the ozone concentration-luminescence response characteristics in the steady state. As long as the ozone concentration-luminescence response characteristics is known, the time characteristics (for example, a time constant) of the luminescence response of this system and the parameter such as the cubic volume of the reactor, the pressure in the reactor and the flow rate of the gas can be obtained easily from the time characteristics within a range where the nitrogen oxide concentration can be accurately measured, namely the light emission can be generated only in the reactor in compliance with the change rate of the ozone concentration. As a result, this nitrogen oxide analyzer can be applied to any analyzer and can be of a highly practical use.

As mentioned above, in accordance with this invention, as long as the change rate of the ozone concentration can be estimated for any model of the nitrogen oxide analyzer in spite of using ozone-containing gas whose ozone concentration is unstable, it is possible to set the parameter such as the cubic volume of the reactor, the pressure in the reactor and the gas flow rate optimally with ease so that the light emission is completed in the reactor certainly so as to make an accurate measurement without making the reactor unnecessarily big nor lessening the gas flow rate.

As a result, it is possible to generate the ozone-containing gas by introducing the atmospheric air directly to the ozone generator, resulting in power-saving due to omission of the dehumidifier or the drier. In addition, it is possible to provide a downsized and accurate nitrogen oxide analyzer that is especially very preferable for a vehicle-mountable use.

DETAILED DESCRIPTION OF THE PREFERRED EMBODIMENTS

An exhaust gas analyzer 100 in accordance with one embodiment of the present claimed invention will be described in detail with reference to the accompanying drawings.

Figure 1:
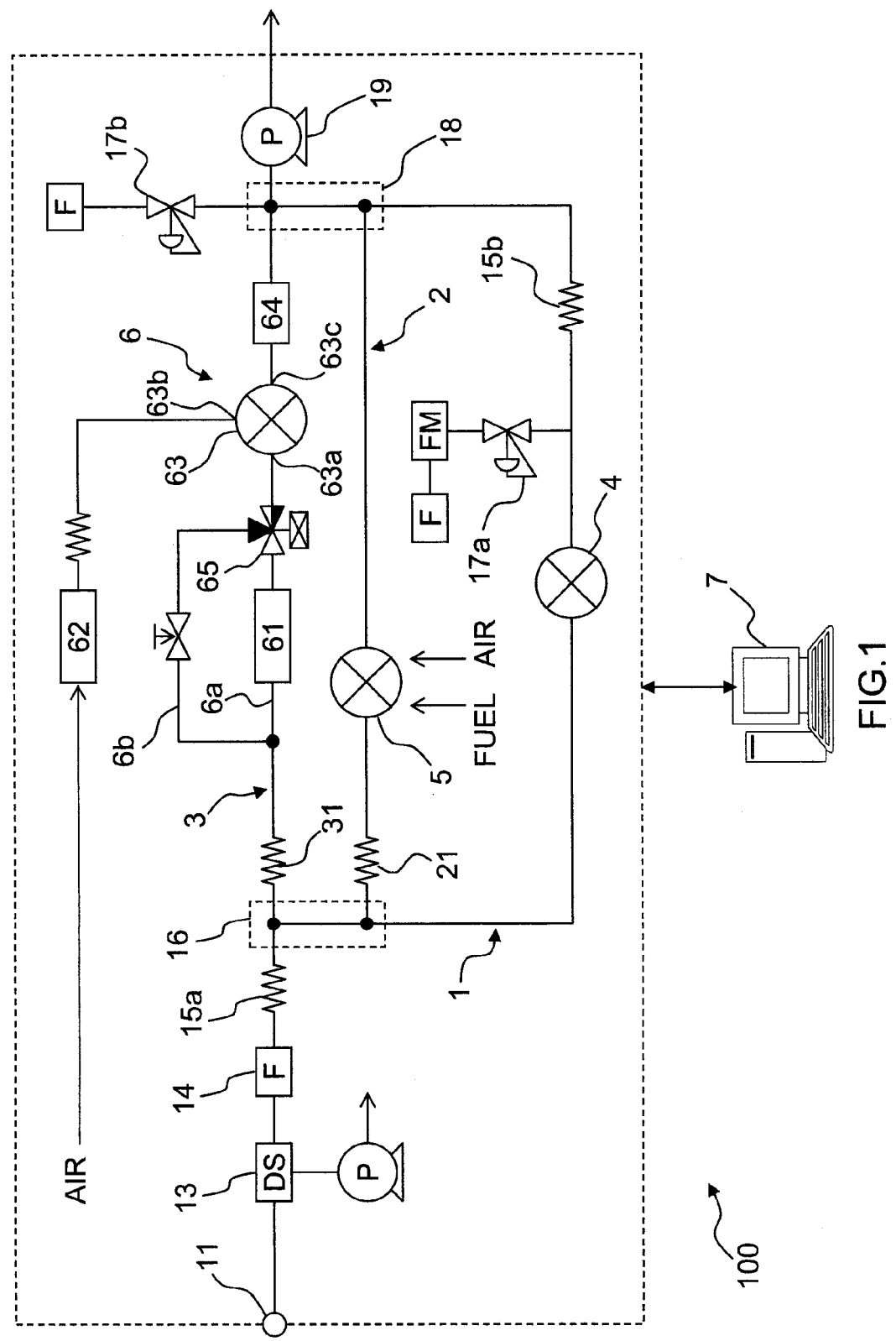
FIG. 1 is an overall fluid circuit diagram of an exhaust gas analyzer in accordance with one embodiment of the present claimed invention.

The exhaust gas measuring system 100 in accordance with this embodiment is to measure concentration of various components in exhaust gas as being sample gas while a vehicle is actually in motion with the exhaust gas measuring system 100 loaded on a trunk of the vehicle and, as shown in FIG. 1, comprises three different analyzers 4, 5, 6, a flow path system for supplying the exhaust gas continuously to the analyzers 4, 5, 6, and an information processing unit 7 that receives actually measured data from each analyzer 4, 5, 6 and analyzes them and that controls a valve arranged in the flow path system.

Each component will be described.

First, an infrared gas analyzer 4 to measure each concentration of CO, $CO_2$, $H_2O$, a hydrogen flame ionization detector 5 to measure concentration of THC, and a chemiluminescent nitrogen oxide analyzer 6 (hereinafter also called as a CLD type $NO_x$ analyzer 6) to measure concentration of $NO_x$ are used as the analyzers 4, 5, 6 in this embodiment.

The infrared gas analyzer 4 is of a nondispersive type and is so arranged to measure light intensity of each wavelength by a photo detector at a time when infrared rays of characteristic wavelength which each CO, $CO_2$, $H_2O$ absorbs passes through the sample gas (the exhaust gas), to output each of them and to compare each of the output values with a reference value at a time when no light is absorbed so that light absorbency of each wavelength can be calculated. The light absorbency of each wavelength shows the concentration of each component of CO, $CO_2$ and $H_2O$.

The hydrogen flame ionization detector 5 is of a type wherein fuel gas is mixed into the sample gas (the exhaust gas) at a constant ratio, the mixed gas is burned in a combustion chamber (a chimney) to which an electric field is applied, electric current generated due to ionization of THC contained in the sample gas is captured, and the electric current is amplified and output. Then the hydrogen flame ionization detector 5 can calculate an amount (concentration) of THC from the output value of the electric current. In addition to the fuel gas, combustion supporting gas (air) also is introduced into the hydrogen flame ionization detector 5.

The CLD type $NO_x$ analyzer 6 can measure an amount (concentration) of $NO_x$ contained in the exhaust gas and comprises an NO converter 61, an ozone generator 62, a reactor 63, and a photo detector (not shown in drawings). The NO converter 61 is to convert $NO_x$ into NO and is arranged at one 6a of a pair of parallel paths 6a, 6b that divide the introduced exhaust gas into two. An electromagnetic switch valve 65 is arranged at a terminal end of the parallel paths 6a, 6b and the exhaust gas is alternatively introduced into the reactor 63 only through either one of the parallel paths 6a, 6b so that the concentration of NO alone contained in the exhaust gas can be measured or the concentration of $NO_x$ except for NO also can be measured by obtaining differences. The ozone generator 62 imports atmospheric air without dehumidification, converts oxygen contained in the atmospheric air into ozone and outputs it as ozone-containing gas. The reactor 63 is a box body having a certain volume and comprises a sample gas introducing port 63a, an ozone-containing gas introducing port 63b and a leading-out port 63c. The gas from either one of the parallel paths 6a, 6b alternatively selected by the switch valve 65 as mentioned above is introduced into the sample gas introducing port 63a and the ozone-containing gas from the ozone generator 62 is introduced into the ozone-containing gas introducing port 63b. Each gas is mixed inside the reactor 63, which causes a chemiluminescent response. The photo detector is to measure the light intensity due to a response in the reactor 63 and, for example, a photoelectron multiplier is used as the photo detector in this embodiment.

The flow path system comprises a main flow path 1 that plays a role as a bypath to pass almost all of the exhaust gas, and multiple (two) sub-flow paths 2, 3 arranged in parallel and bifurcated from the main flow path 1. The infrared gas analyzer 4 is arranged on the main flow path 1, the hydrogen flame ionization detector 5 is arranged on one of the sub-flow paths 2 (a first sub-flow path 2) and the CLD type $NO_x$ analyzer 6 is arranged on other sub-flow path 3 (a second sub-flow path 3) respectively.

An upstream end of the main flow path 1 opens as a main port 11 and a suction pump 19 is arranged at the most downstream side of the main flow path 1. An exhaust duct of a vehicle is connected to the main port 11 and an amount of the exhaust gas required for measurement is introduced into the main flow path 1 by sucking the exhaust gas by the use of the suction pump 19.

More concretely, in succession to the main port 11 a drain separator 13 to remove liquid moisture contained in the exhaust gas, a filter 14, a flow rate control pipe (capillary) 15a, a bifurcated part 16, the infrared gas analyzer 4, a flow rate control pipe (capillary) 15b, an interflow part 18, the suction pump 19 are arranged serially in this order. Since portions from the exhaust duct of the vehicle to the drain separator 13 are connected with an unheated piping alone at least without using a heated piping, the exhaust gas is introduced into each analyzer 4, 5, 6 in a state wherein only liquid moisture is removed by the drain separator 13 (hereinafter also called as a semi-dry state). A pressure control valve 17a connected downstream of the infrared gas analyzer 4 is to control pressure in the flow path system between the capillaries 15a and 15b, and serves as a role to hold a flow rate and pressure of the exhaust gas flowing into the infrared gas analyzer 4 constant in cooperation with each capillary 15, 15b.

The sub-flow paths 2, 3 are so arranged to be bifurcated from the main flow path 1 at the bifurcated part 16 and to be connected to the main flow path 1 again at the interflow part 18.

A flow rate control pipe (capillary) 21 and the hydrogen flame ionization detector 5 are arranged in this order on the first sub-flow path 2. The flow rate control pipe 21 is to limit an amount of gas that flows into the first sub-flow path 2 to a flow rate (very small amount compared with the flow rate of the exhaust gas that flows into the main flow path 1) necessary for measuring concentration of THC.

A flow rate control pipe (capillary) 31 and the CLD type $NO_x$ analyzer 6 are arranged in this order from upstream on the second sub-flow path 3. The flow rate control pipe (capillary) 31 is to limit an amount of gas that flows into the second sub-flow path 3 to a flow rate (very small amount compared with the flow rate of the exhaust gas that flows into the main flow path 1) necessary for measuring concentration of $NO_x$.

The pressure control valve 17b connected to the interflow part 18 is to control pressure of each sub-flow path 2, 3, and serves as a role to hold a flow rate and pressure of the exhaust gas flowing into the hydrogen flame ionization detector 5 and the CLD type $NO_x$ analyzer 6 constant in cooperation with each capillary 21, 22 arranged upstream of each sub-flow path 2, 3.

Figure 2:
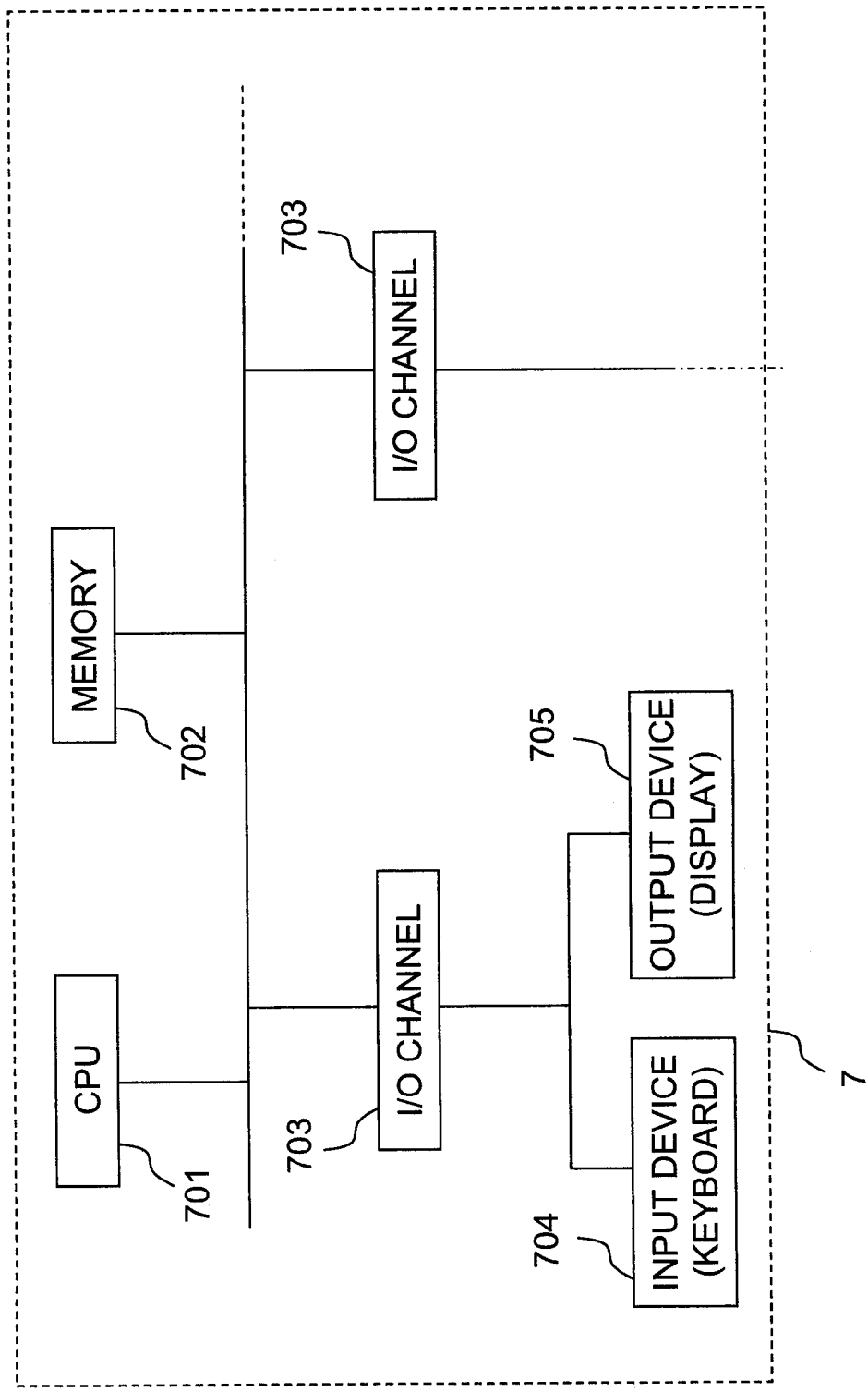
FIG. 2 is a circuit structure diagram of an information processing unit in accordance with this embodiment.

The information processing unit 7 is, as shown in FIG. 2, of multi-purpose or exclusive use comprising a CPU 701, a memory 702, an input/output channel 703, an input device 704 such as a keyboard, and a display 705. An analog-digital converting circuit such as an A/D converter, a D/A converter, and an amplifier (not shown in drawings) arranged at a side of the analyzers is connected to the input/output channel 703. The information processing unit 7 at least fulfills function as a controlling part that controls the valve arranged on the flow path system to open or close or temperature of a heater, and an analyzing part that receives detected data output from each analyzer 4, 5, 6 and analyzes them so as to calculate concentration of each component by a cooperative action of the CPU 701 and its peripheral equipment according to a program stored in a predetermined area of the memory 72. The information processing unit 7 is not necessarily integrated physically, and may be separated into multiple instruments connected by a fixed line or wireless.

In this embodiment, as mentioned above, since the CLD type $NO_x$ analyzer 6 is so arranged that atmospheric air is introduced into the ozone generator 62 without dehumidification, a dehumidifier and a drier that are necessary for a conventional analyzer can be omitted. This arrangement makes it possible to reduce electrical consumption to a large extent and to downsize the analyzer, resulting in facilitating this analyzer being loaded on a vehicle.

As mentioned above if the atmospheric air is directly introduced into the ozone generator 62, the ozone concentration in the ozone-containing gas output from the ozone generator 62 fluctuates due to fluctuation of oxygen concentration when humidity in the atmospheric air fluctuates. As a result, a measurement error of the nitrogen oxide might be generated.

Then, in this embodiment, a relationship between the cubic volume of the reactor 63, the pressure in the reactor 63, the flow rate of introducing the sample gas into the reactor 63 and the flow rate of introducing the ozone-containing gas into the reactor 63 is so set that the response of light emission is completed in the reactor 63, even though the ozone concentration fluctuates within an expected range, so that the fluctuation of the ozone concentration does not have an impact on the measurement value or the impact can be reduced as much as possible.

More concretely, for better understanding, a relationship between the light intensity, the concentration of NO or ozone, or the time period of light emission will be explained prior to explaining the method.

When nitric oxide reacts with ozone, nitrogen peroxide ($NO_2$) is generated and a part of the generated nitrogen peroxide becomes excitation $NO_2$ at a certain ratio. When excitation $NO_2^*$ returns to a base state, the excitation energy is released as the light energy as shown in equation (2). A process of the light emission is expressed by the following chemical equation.

$$k_2$$
$$NO+O_3 \rightarrow NO_2^* + O_2 \quad (1)$$

$$k_3$$
$$NO_2^* \rightarrow NO_2 + h\nu \quad (2)$$

$$k_4$$
$$NO_2^* + M \rightarrow NO_2 + M^* \quad (3)$$

Where each of $k_2$, $k_3$, $k_4$ is a constant that defines the velocity of each response.

The velocity of decreasing NO during a process of equation (1) through equation (3) is expressed by the following equation (4).

$$-d[NO]/dt = k_2[NO][O_3] \quad (4)$$

Where [ ] expresses the concentration.

Since a generating amount of $NO_2^*$, namely the concentration of $NO_2^*$ is an amount that a current amount of the NO concentration is subtracted from an initial value of the NO concentration, the generating amount of $NO_2^*$ is expressed by the following equation (5).

$$[NO](0) - [NO] = [NO_2^*] \quad (5)$$

Where, [NO] (0) is an initial value of the NO concentration.

The response of the light emission expressed by the equation (2) is generated at a certain ratio (there might be a case that a response of the light emission is not generated at a certain ratio due to a quenching phenomenon expressed by the equation (3)) every time $NO_2^*$ is generated due to the chemical response expressed by the equation (1), and since the light intensity I is an integral value of a single shot of the light emission due to the response, the light intensity I is proportional to an amount of generated $NO_2^*$, namely the concentration of $NO_2$. The light intensity I is expressed by the following equation (6).

$$I = A_1 \cdot [NO_2] \quad (6)$$

Where $A_1$ is a proportionality constant.

Then the light intensity I is obtained from a relationship between the time t and the concentration of $O_3$ by the following equation (7).

$$I = A \cdot \{1 - \exp(-k_2 \cdot [O_3] \cdot t)\} \quad (7)$$

Where $A = A_1 \cdot [NO] (0)$

As is clear from the equation (7), a time constant τ of the light emission system is expressed by the following equation (8).

$$\tau = 1/(k_2 \cdot [O_3]) \quad (8)$$

As a result, $k_2$ can be considered to be a characteristic value that is intrinsic to the light emission system that specifies the time constant.

Then in this embodiment, a steady state (each of the concentration, the flow rate and the pressure of the gas is kept constant) is produced, t is kept at a certain value Tc (the gas average residence time in the reactor 63 is kept constant), then only the concentration of $O_3$ is varied in the steady state and finally $k_2$ is obtained based on the change of the light intensity I at that time.

Conversely, in this embodiment, the light emission is completed in the reactor 63 even though the ozone concentration fluctuates in some degree and the concentration of NO can be obtained uniquely from the light intensity by setting a parameter that specifies the gas average residence time t in the reactor 63, namely a relationship between the cubic volume of the reactor 63, the pressure in the reactor 63, the flow rate of introducing the sample gas into the reactor 63, the flow rate of introducing the ozone-containing gas into the reactor 63.

A method will be described as follows.

First, the reference sample gas containing nitrogen oxide (in this embodiment, NO) with constant concentration and the reference ozone-containing gas with known concentration pass at a certain amount instead of the exhaust gas and the ozone-containing gas, and the pressure in the reactor 63 is kept constant (a step to produce the steady state).

In this steady state, the average period Tc while the mixed gas resides in the reactor 63 is a constant value obtained by the following equation (10).

$$Tc = Vc \times Pc/Qc \quad (10)$$

Where Vc is the cubic volume of the reactor 63, Pc is the pressure in the reactor 63 in the steady state and Qc is the total amount of the gas flowing into the reactor 63 in the steady state.

Figure 3:
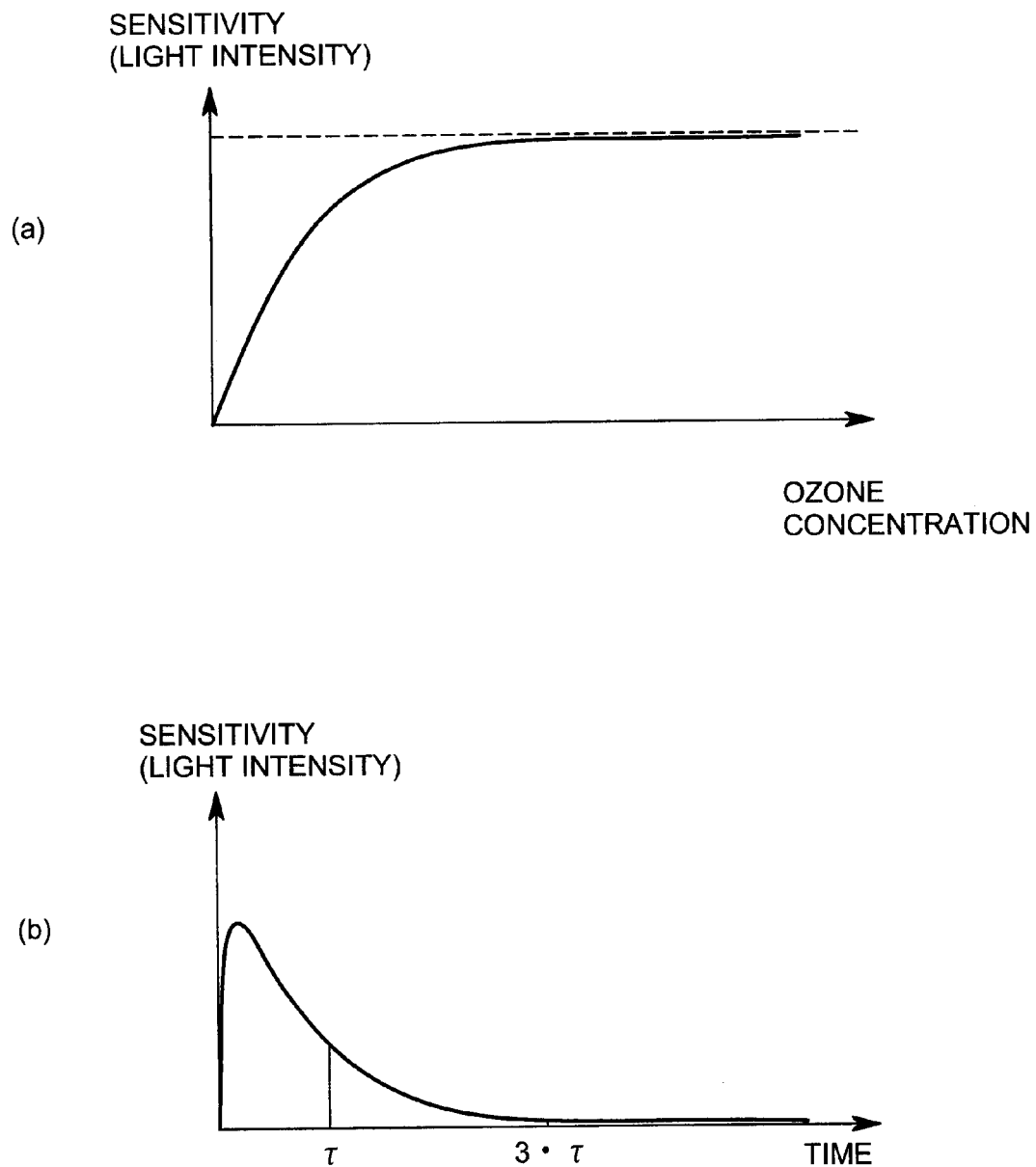
FIG. 3 is a graph showing a relationship between light intensity and ozone concentration and a relationship between light intensity and time in accordance with this embodiment.

A relationship between the light intensity (sensitivity) I in the steady state and the ozone concentration $[O_3]$ is expressed by the following equation (11) obtained from the equations (7) and (10). A graph wherein the horizontal axis is the ozone concentration $[O_3]$ and the vertical axis is the light intensity (sensitivity) I is shown in FIG. 3(a).

$$I = A(1 - \exp(-k_2 \cdot Tc \cdot [O_3])) \quad (11)$$

Where $A = A_1 \cdot [NO] (0)$

Next, the ozone concentration alone is changed and a changed value of the light intensity corresponding to it is detected, and then response characteristics of the ozone concentration-light emission that shows a relationship between the ozone concentration and the light intensity, namely the chemiluminescent response is obtained. More concretely, a point where a change amount of the light intensity corresponding to a rising amount of the ozone concentration becomes less than or equal to a predetermined minute amount, namely a point where a change of sensitivity becomes almost nothing is obtained by raising the ozone concentration gradually so as to increase the response speed of $NO + O_3$ (a step to obtain the response characteristics).

More concretely, if the point is set as a point of about 95% of a saturation value of the light intensity and the point is conceived to be a point where the time when the response of $NO + O_3$ completes generally equals to the time when the sample gas passes, a following equation (12) can be derived.

$$3\tau = Tc \quad (12)$$

If the equation (8) and the equation (10) are substituted to the equation (12), the equation (13) is derived and the characteristic value $k_2$ can be obtained.

$$k_2 = 3/([O_3]_c \times Vc \times Pc/Qc) \quad (13)$$

Where $[O_3]_c$ is a value of the ozone concentration at a time when the change of the light intensity becomes equal to or less than the predetermined minute amount. In addition, τ is tripled in the equation (12), however, it is an example of a case where the point is set as the point of about 95% of the saturation value, and it is not limited to this.

In addition, the ozone concentration only is changed and each value of the light intensity corresponding to multiple values of the ozone concentration is detected, and then the equation (11) as being the response characteristics is specified so that each value of the light intensity falls on each point, for example, by the use of the least-square method (the step to obtain the response characteristics). $K_2$ as being a characteristic value of this measuring system may be obtained by the specified equation (11).

Finally, the relationship of the cubic volume V of the reactor 63, the pressure P of the reactor 63, the flow rate Q of introducing the sample gas and the ozone-containing gas into the reactor 63 is set so that the response of the light emission is generated only in the reactor 63 even though the ozone concentration of the ozone-containing gas varies within the predetermined range based on thus obtained characteristic value $k_2$ (a step to set the parameter).

More concrete explanation is as follows.

As is clear from the equation (7), the saturation value of the light intensity (sensitivity) I is $A = A_1 \cdot [NO] (0)$, and the value to be obtained as the sensitivity is the concentration of NO, namely $[NO] (0)$. As a result, the bigger a value of τ, the less an effect on the light intensity (sensitivity) I due to fluctuation of the value of t.

Then in this embodiment, in order not to lose measurement accuracy in spite of fluctuation of the ozone concentration, the average period while the mixed gas resides in the reactor 63 $t_O = V \times P/Q$ is defined based on the time constant τ $(=1/(k_2 \cdot [O_3]))$ so that the measurement accuracy is within almost an unsusceptible range even though the time constant τ changes because the ozone concentration fluctuates a little from the reference value, since the time constant τ of this graph can be expressed as $1/(k_2 \cdot [O_3])$ from the equation (8). As mentioned in the equation (14), $t_Q$ is defined to be equal to or more than n times of I (more concretely, triple of 95% of the saturation value).

$$3\cdot\tau \leq t_Q = V \times P/Q \qquad (14)$$

FIG. 3(b) shows a time change of the light intensity when a predetermined amount of NO is introduced into the reactor 63 in an impulse form. As is clear from FIG. 3(b), that the average period $t_Q$ is set more than or equal to triple of τ shows that almost all (more than or equal to 95%) of one cycle of the light emission is brought to completion within the period $t_Q$.

It is a matter of course that the average period $t_Q$ has to be set more than or equal to triple of τ when a fluctuation range of the ozone concentration is big. Conversely, it may be less than triple of τ when a fluctuation range of the ozone concentration is not big. To be brief, the average period $t_Q$ may be estimated to be more than or equal to n times of τ in compliance with the fluctuation range of the ozone concentration. The ozone concentration $[O_3]$ at a time of defining I may be set to be, for example, a center value of the fluctuation range.

Since the cubic volume V of the reactor 63 can not be changed after the CLD type $NO_x$ analyzer is completed, the pressure P or the flow rate Q is set by adjusting the pressure control valve or the capillary so as to meet the average period $t_Q$ obtained by the equation (14) and the relationship of the cubic volume V of the reactor 63, the pressure P in the reactor 63, and the flow rate Q of introducing the gas into the reactor 63 are set. In addition, also the cubic volume V of the reactor 63 may be adjusted at a stage of designing or developing the analyzer.

As mentioned above, in accordance with this embodiment, no matter how complicated the system is, it is not very difficult to produce the steady state. As a result of this, the characteristic value $k_2$ can be obtained easily from the change of the ozone concentration and the change of the light intensity in the steady state.

It is possible to set the relationship of the cubic volume V, the pressure P and the flow rate Q easily so that the luminescence response is brought to completion in the reactor 63 without fail as long as the change rate can be estimated by the use of the characteristic value $k_2$ even though the ozone concentration of the ozone-containing gas changes, thereby making it possible to measure the concentration of NO with accuracy by lessening the measurement error.

In addition, since the concentration of NO can be measured with accuracy even though the concentration of ozone is unstable, it is possible to introduce the atmospheric air without dehumidification directly into the ozone generator 62. As a result, power-saving or downsizing due to omission of the dehumidifier or the drier makes it possible to provide a real time nitrogen oxide analyzer especially very preferable for a vehicle-mountable use.

The present claimed invention is not limited to the above-mentioned embodiment.

For example, the information processing unit 7 may automatically obtain the response characteristics or calculate the parameter.

More concretely, a predetermined installation program is installed on the information processing unit 7 and the information processing unit 7 serves as the following functions in cooperation with a CPU 701, a memory 702, and peripheral devices based on the installation program.

Figure 4:
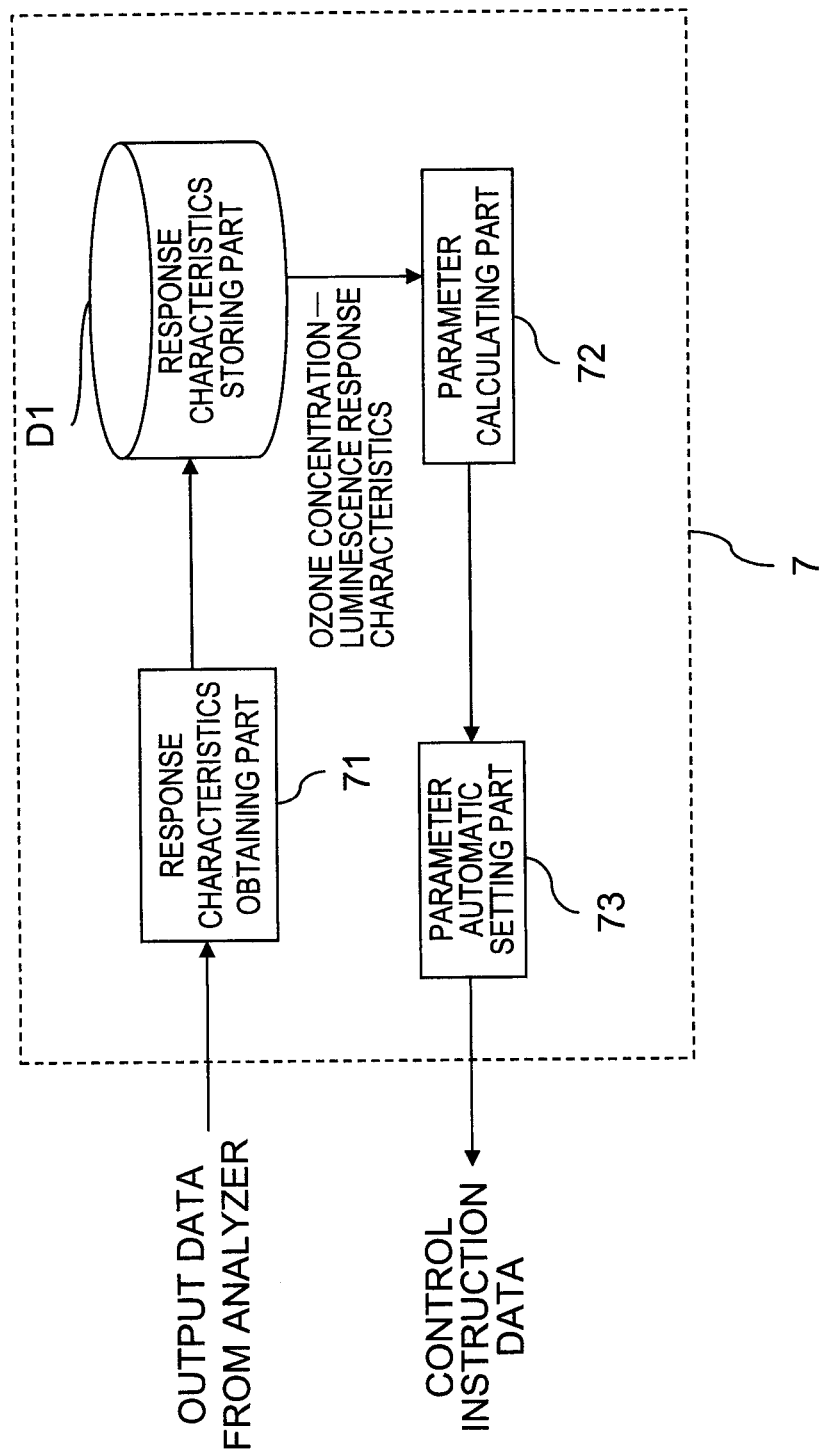
FIG. 4 is a functional block diagram of the information processing unit in accordance with this embodiment.

More specifically, as shown in FIG. 4, the information processing unit 7 functions as a response characteristics obtaining part 71 that obtains ozone concentration-luminescence response characteristics as being the relationship between the ozone concentration and the light intensity by the chemiluminescent response obtained by varying the ozone concentration alone in the steady state and that memorizes it in the response characteristics storing part D1, and as a parameter calculating part 72 that calculates a relationship of the parameter (the cubic volume of the reactor 63, the pressure of the reactor 63, the flow rate of the sample gas introducing into the reactor 63, the flow rate of the ozone-containing gas introducing into the reactor 63) that determines an average resident time of the sample gas in the reactor 63 so that the luminescence response is generated only in the reactor 63 even though the ozone concentration of the sample gas changes within a predetermined range based on the ozone concentration-luminescence response characteristics.

As is the case with the step to set the parameter, the parameter calculating part 72 calculates the characteristic value $k_2$ based on the ozone concentration-luminescence response characteristics memorized in the response characteristics storing part D1, and calculates the relationship of the parameter based on the characteristic value $K_2$.

Furthermore, a parameter automatic setting part 73 may be arranged on the information processing unit 7. The capillary and the pressure control valve can be controlled by the information processing unit 7, a pressure sensor or a flow rate sensor that measures the pressure P in the reactor 63, the flow rate Q of the sample gas and the ozone-containing gas introduced into the reactor 63 is arranged, the measured information is transmitted to the information processing unit 7, and the capillary or the pressure control valve is controlled based on the calculated result of the parameter calculating part 72. The other arrangement of the component is not limited to the embodiment described in drawings and there may be various modifications without departing from the spirit of the invention.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

The invention claimed is:

1. A parameter setting method that is applied to a nitrogen oxide analyzer including a reactor in which an ozone-containing gas and a sample gas containing nitrogen oxide continuously introduced in a time-series order are mixed and the mixed gas is passed out through an output port, and a photo detector that detects a light intensity of chemiluminescence caused by the mixing, wherein the concentration of nitrogen oxide in the sample gas can be calculated based on the light intensity detected by the photo detector, the method comprising:

producing a steady state by flowing a reference sample gas whose nitrogen oxide concentration is kept constant and a reference ozone gas whose ozone concentration is known at a constant flow rate instead of the sample gas and the ozone-containing gas respectively and by making the pressure in the reactor constant;

gradually changing the ozone concentration alone in the steady state;

obtaining a specific ozone concentration as being an ozone concentration in case that a change amount of the light intensity corresponding to the change of the ozone concentration becomes less than or equal to a predetermined minute amount;

calculating a value that specifies a chemiluminscent response time constant intrinsic to the reactor and that determines a velocity of a response between nitrogen oxide and ozone based on the specific ozone concentration; and setting a relationship of parameters that determines an average resident time of the sample gas in the reactor so that the luminescence response is generated almost only in the reactor even though the ozone concentration of the ozone-containing gas changes within a predetermined range based on the value, wherein the parameters include the cubic volume of the reactor, the pressure in the reactor, the flow rate of the sample gas introduced into the reactor, and the flow rate of the ozone-containing gas introduced into the reactor.

2. The parameter setting method that is applied to the nitrogen oxide analyzer of claim 1, wherein a characteristic value that specifies a chemiluminescent response time constant intrinsic to the nitrogen oxide analyzer is calculated based on the specific ozone concentration and the relationship of the parameters is set based on the characteristic value.

3. The parameter setting method that is applied to the nitrogen oxide analyzer of claim 2, wherein the characteristic value is calculated from the specific concentration of ozone, the cubic volume of the reactor, the pressure in the reactor, and the flow rate of the ozone containing gas and the sample gas introducing into the reactor.

4. A nitrogen oxide analyzer comprising:
a reactor in which an ozone-containing gas and a sample gas containing nitrogen oxide continuously introduced in a time-series order are mixed and the mixed gas is passed out through an output port;
a photo detector that detects a light intensity of chemiluminescence caused by the mixing; and
an information processing unit that calculates concentration of nitrogen oxide in the sample gas based on the light intensity detected by the photo detector, wherein the information processing unit comprises
a response characteristics obtaining part that (i) produces a steady state by flowing a reference sample gas whose nitrogen oxide concentration is kept constant and a reference ozone gas whose ozone concentration is known at a constant flow rate instead of the sample gas and the ozone-containing gas respectively and by making the pressure in the reactor constant, (ii) gradually changes the ozone concentration alone in the steady state, (iii) obtains a specific ozone concentration as being an ozone concentration in case that a change amount of the light intensity corresponding to the change of the ozone concentration becomes less than or equal to a predetermined minute amount, and (iv) calculates a value that specifies a chemiluminescent response time constant intrinsic to the reactor and that determines a velocity of a response between nitrogen oxide and ozone based on the specific ozone concentration, and
a parameter calculating part that sets a relationship of parameters that determines an average resident time of the sample gas in the reactor so that the luminescence response is generated almost only in the reactor even though the ozone concentration of the ozone-containing gas changes within a predetermined range based on the value, wherein the parameters include the cubic volume of the reactor, the pressure in the reactor, the flow rate of the sample gas introduced into the reactor, and the flow rate of the ozone-containing gas introduced into the reactor.

5. The nitrogen oxide analyzer of claim 4, wherein the parameter calculating part calculates a characteristic value that specifies a chemiluminescent response time constant that is intrinsic to the nitrogen oxide analyzer based on the ozone concentration-luminescence response characteristics, and calculates the relationship of the parameters based on the characteristic value.

6. The nitrogen oxide analyzer of claim 4, wherein the response characteristics obtaining part specifies a time when the change amount of the light intensity relative to a predetermined change amount of the ozone concentration becomes less than or equal to a predetermined minute amount as the ozone concentration-luminescence response characteristics; and
the parameter calculating part calculates the characteristic value from the cubic volume of the reactor, the pressure in the reactor and the flow rate of introducing the sample gas and the ozone-containing gas into the reactor.

7. The nitrogen oxide analyzer of claim 4, wherein the response characteristics obtaining part detects each value of the light intensity corresponding to multiple values of the ozone concentration, and obtains the ozone concentration-luminescence response characteristics as being a relational equation between the ozone concentration and the light intensity that almost satisfies each detected value of the light intensity.

8. A vehicle-mountable nitrogen oxide analyzer comprising:
a reactor where ozone-containing gas and exhaust gas continuously introduced in a time-series order are mixed and the mixed gas is passed out through an output port;
a photo detector that detects intensity of light generated in the reactor by mixing the ozone-containing gas and the exhaust gas;
an information processing unit that calculates the nitrogen oxide concentration in the exhaust gas based on the light intensity detected by the photo detector; and
an ozone generator that introduces atmospheric air without dehumidification and that generates the ozone-containing gas by converting oxygen in the atmospheric air into ozone, wherein the introduction of ozone-containing gas and exhaust gas containing nitrogen oxide into the reactor is based on a relationship between parameters including reactor volume, exhaust gas flow rate, ozone-containing gas flow rate and gas pressure in the reactor and a calculated value that specifies a chemiluminescent response time constant intrinsic to the reactor that determines a velocity response between nitrogen oxide and a specific ozone concentration such that an average resident time of the exhaust gas in the reactor allows light generation to occur substantially only in the reactor as the ozone concentration changes within a predetermined range from the specific ozone concentration.

* * * * *